United States Patent
Zhou et al.

(10) Patent No.: US 10,490,108 B2
(45) Date of Patent: Nov. 26, 2019

(54) ITEM LABEL WITH A TAG

(71) Applicant: TruTag Technologies, Inc., Kapolei, HI (US)

(72) Inventors: Ting Zhou, Orinda, CA (US); Timothy Learmonth, Berkeley, CA (US); Michael P. O'Neill, Kaneohe, HI (US); Peter Pearson, Aptos, CA (US)

(73) Assignee: TruTag Technologies, Inc., Kapolei, HI (US)

(*) Notice: Subject to any disclaimer, the term of this patent is extended or adjusted under 35 U.S.C. 154(b) by 0 days.

(21) Appl. No.: 15/423,337

(22) Filed: Feb. 2, 2017

(65) Prior Publication Data
US 2017/0206809 A1    Jul. 20, 2017

Related U.S. Application Data

(62) Division of application No. 13/158,254, filed on Jun. 10, 2011, now abandoned.
(60) Provisional application No. 61/354,639, filed on Jun. 14, 2010.

(51) Int. Cl.
| G09F 3/00 | (2006.01) |
| B42D 25/28 | (2014.01) |
| B42D 25/22 | (2014.01) |
| G06F 19/00 | (2018.01) |

(52) U.S. Cl.
CPC .......... G09F 3/0297 (2013.01); B42D 25/22 (2014.10); B42D 25/28 (2014.10); G06F 19/3462 (2013.01); B42D 2035/12 (2013.01); B42D 2035/34 (2013.01); B42D 2035/50 (2013.01)

(58) Field of Classification Search
CPC ... G09F 3/0297; G06F 19/3462; B42D 25/22; B42D 25/28
USPC .............. 283/67, 70, 72, 74, 79, 81, 98, 901
See application file for complete search history.

(56) References Cited

U.S. PATENT DOCUMENTS

| 6,799,725 | B1 | 10/2004 | Hess |
| 7,089,420 | B1 | 8/2006 | Durst |
| 7,543,745 | B1 | 6/2009 | Simske |
| 7,581,242 | B1 | 8/2009 | Oget |
| 7,903,338 | B1 | 3/2011 | Wach |
| 2003/0174326 | A1 | 9/2003 | Rzasa |
| 2006/0020469 | A1 | 1/2006 | Rast |
| 2006/0086791 | A1 | 4/2006 | Austin |
| 2006/0118739 | A1 | 6/2006 | Ross |
| 2006/0174129 | A1 | 8/2006 | Brignone |
| 2006/0206714 | A1* | 9/2006 | Gubo ............... G06K 17/00 713/176 |
| 2007/0205284 | A1 | 9/2007 | Ross |
| 2008/0093448 | A1 | 4/2008 | De La Huerga |
| 2008/0129037 | A1 | 6/2008 | Roth |

(Continued)

FOREIGN PATENT DOCUMENTS

CN    101136076    3/2008

OTHER PUBLICATIONS

Hongjuan Li, "Software Analysis and Design on RFID Label Data Reading and Writing" Journal of Jilin Institute of Chemical Technology, No. 2, vol. 25.

*Primary Examiner* — Justin V Lewis
(74) *Attorney, Agent, or Firm* — Van Pelt, Yi & James LLP

(57) ABSTRACT

A label has a portion that is readable by a human being and a portion that is readable by a machine. The label includes information stored using a spectral content of reflected from a tag. The label is used for authentication.

15 Claims, 7 Drawing Sheets

(56) References Cited

U.S. PATENT DOCUMENTS

| | | |
|---|---|---|
| 2008/0252066 A1 | 10/2008 | Rapoport |
| 2008/0262768 A1 | 10/2008 | Ramsden |
| 2009/0008924 A1 | 1/2009 | Ophey |
| 2009/0021788 A1 | 1/2009 | Hoffman |
| 2009/0309733 A1 | 12/2009 | Moran |
| 2011/0258130 A1* | 10/2011 | Grabiner .............. G06Q 10/087 705/317 |

* cited by examiner

ITEM LABEL WITH A TAG

CROSS REFERENCE TO OTHER APPLICATIONS

This application is a divisional of co-pending U.S. patent application Ser. No. 13/158,254, entitled LABELING AND VERIFYING AN ITEM WITH AN IDENTIFIER filed Jun. 10, 2011 which is incorporated herein by reference for all purposes, which claims priority to U.S. Provisional Application No. 61/354,639 entitled LABELING AND VERIFYING AN ITEM WITH AN IDENTIFIER filed Jun. 14, 2010 which is incorporated herein by reference for all purposes.

BACKGROUND OF THE INVENTION

A producer or reseller of items (including ingredients and components of such items)—for example a manufacturer, but also including other parties in the entire supply and distribution chain such as a supplier, a wholesaler, a distributor, a repackager, and a retailer—especially, but not limited to, high-value items, faces counterfeiting of the item. Counterfeiting includes the substitution, dilution, addition or omission of ingredients or components of the item compared to its intended product specification, as well as misrepresentation or diversion of the packaged item from its intended course of sale. This leads to loss of potential revenue as counterfeit items are sold in the place of the real item. Also, there can be health or product related damages caused by not using an authentic item as opposed to a counterfeit—for example, the counterfeit can perform differently or not at all as compared to an authentic item. This is particularly acute in industries that can affect health and safety such as industries involved with pharmaceuticals, nutritional supplements, medical devices, food and beverages, construction, transportation, and defense.

As international criminal organizations become more sophisticated, existing packaging security is proving inadequate. The complexity of many industry supply chains—for example, the supply chain of the pharmaceutical industry—lends itself to entry points for adulterated or counterfeit product(s), often found in carefully counterfeited and high-quality packaging, and sometimes in authentic packaging that has either been stolen or as part of a repackaging operation.

In complex product supply chains and markets with variable pricing, opportunities for arbitrage exist for unscrupulous parties to misrepresent product pricing without any change to the underlying product, and thus benefit monetarily, for example, as in returns, rebate or charge-back fraud. Monetary gain or loss to either side of a transaction may also result from errors in record-keeping.

In addition to counterfeiting or product misrepresentation, items that appear physically identical or similar, for example certain nutritional supplements, may actually contain different ingredients or components, but because of similar appearance may be unintentionally packaged or labeled incorrectly. Even if the items are otherwise identical, they may have different properties associated with the particular lot or batch conditions; for example, pharmaceuticals that otherwise appear identical may have different expiration dates and be incorrectly labeled due to failures or limitations in quality assurance protocols to ascertain such differences.

For product development and research, it may be beneficial at times to study and authenticate performance of items that appear identical but are made differently to learn whether or how those differences affect an end use. At times, it is important in such studies—for example in clinically masked (or 'blind') studies leading to pharmaceutical development—to be able to confidently identify the underlying item without revealing the true identity to study participants. In the case of pharmaceutical development and clinical trials, item-level identity error may be introduced, for example, at the contract research organization that repackages the various product formulations into masked unit-doses. Much time, cost, and effort goes into statistical sampling and chemical analyses to verify the true identity of the unit-doses that are ultimately administered.

In the effort to attain positive health outcomes in a more cost-effective and timely manner, healthcare providers need to focus on the adherence to health regimens, not just the efficacy of specific drugs. Understanding when, where and how often medicine is prescribed by a doctor, accurately and timely dispensed from a pharmacy, received by a patient, and consumed by the patient is helpful in understanding and verifying the effectiveness of the overall health regimen. Recording and collecting the data for appropriate analysis and study while also being able to confirm the underlying identity of the medicine at each stage is important to the reliability of the information collected.

BRIEF DESCRIPTION OF THE DRAWINGS

Various embodiments of the invention are disclosed in the following detailed description and the accompanying drawings.

DETAILED DESCRIPTION

Figure 1:
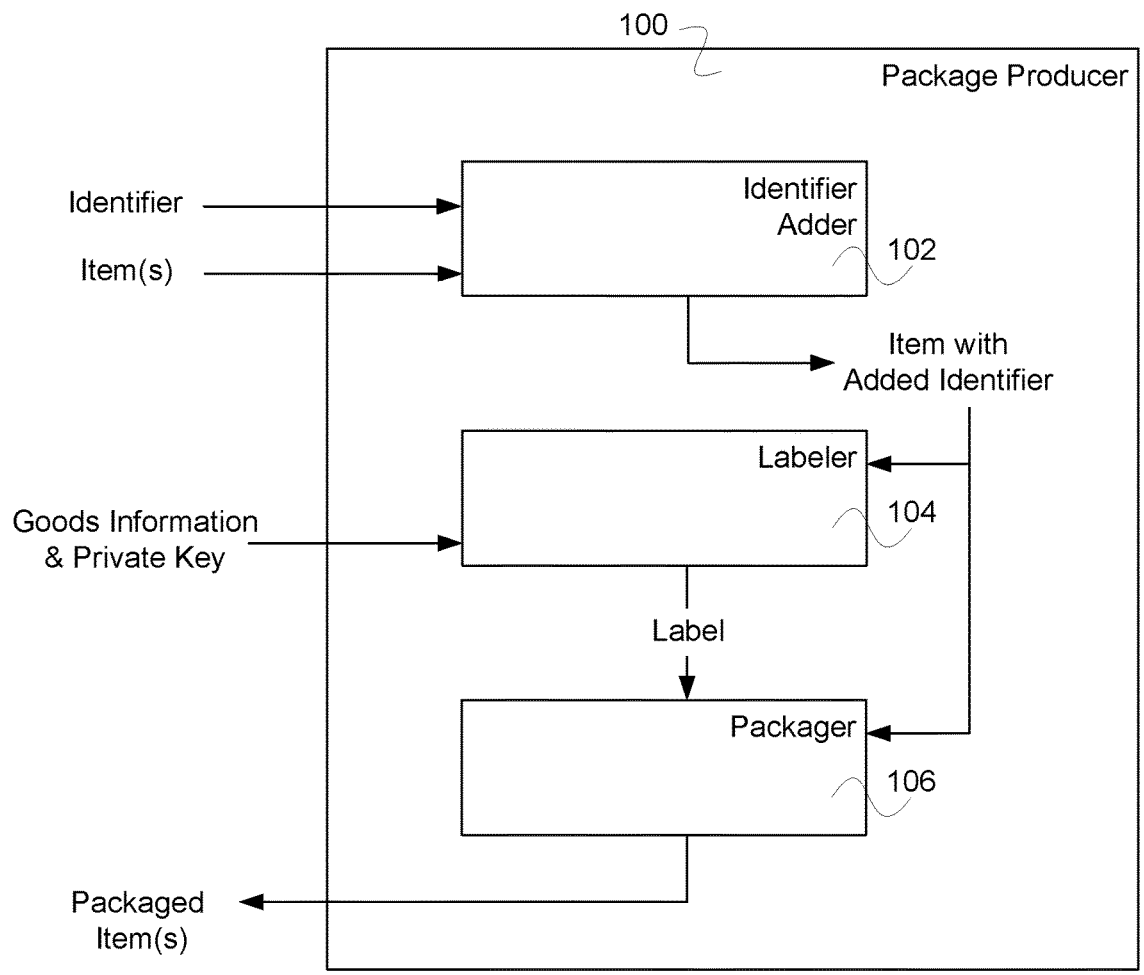
FIG. 1 is a block diagram illustrating an embodiment of a package producer.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for labeling and verifying an item with an identifier is disclosed. The system comprises a package producer and a verifier. The package producer produces a package with a label. The package includes one or more items each with an associated one or more selected tag identifiers that are placed in a location on the item. The verifier verifies the one or more items using 1) the associated one or more selected tag identifiers as detected using a spectral measurement or 2) the location and/or shape of the tag identifiers on the item as detected using an imager, and 3) the label as read using a label reader.

In various embodiments, the package contains individually identified items, the package contains one type of item identified with an identifier for the one type of item, or any other appropriate mapping of identifier(s) and/or item type, or any appropriate item or type of item. For example, each item (e.g., an individual art piece) has an individually identifiable set of tags or each type of item (e.g., all art pieces of a series of art pieces, a series of lithographic reproductions, etc.) has the same tag. So, that either each individual item is identifiable because it has a different tag, or all the items of the same type have the same tag so that the items of the type cannot individually be told apart but instead can be differentiated from other types of items (e.g., vitamin C tablets as opposed to vitamin D, or a low-dose type of medicine opposed to its higher-dose counterpart, etc.).

In various embodiments, the label is comprised in part of information about the packaged items (hereby denoted goods information or goods info) that is useful to authenticate with the item. For example, goods info for medicines may contain dosage information, expiration dates, lot numbers, etc. Goods information may comprise different types of information depending on the associated item—for example, ingredient(s), SKU number, identifier, physical characteristic (e.g., weight, dimension, volume, etc.), nutrition information, etc.

In various embodiments, the package comprises a pharmaceutical package that includes one or more solid oral dosage forms (SODFs: e.g., tablets, capsules, caplets, powders, crystals, and thin films, etc.), liquids (e.g., creams, gels, liniments, balms, lotions, injectables, and ointments, etc.), and/or any other appropriate medicines. The medicines have one or more added tag identifiers that are added into the outer coating, are distributed on the outer layer of an uncoated medicine (e.g., a SODF), are distributed throughout a SODF or liquid, or any other appropriate manner of adding a tag identifier. In some embodiments, each tag comprises a rugate filter. In some embodiments, the physical placement is used for identification—for example, the tags are laid out in a pattern (e.g., geometric shape, bar code, etc.) that is detectable using an imaging device. In some embodiments, the shapes of the tags are characterized and the characterization is used for identification.

In various embodiments, the package comprises a pharmaceutical package that includes one or more pills, liquids, test strips, transdermal patches or any other appropriate medicines or medical devices. The medicines have an added tag identifier that is added into the outer coating, is distributed on the outer layer of an uncoated medicine (e.g., a pill), is distributed throughout a pill or liquid, or any other appropriate manner of adding a tag identifier. In various embodiments, the package comprises an item—for example, an electronic chip, sub-component, medical devices, an automobile or airplane part, building or material supplies, clothing, toys, cosmetics, jewelry, watches, works of art, currency, tickets, official identification documents, wine, or gourmet food. In some embodiments, the tag comprises a rugate filter. In some embodiments, the physical placement is used for identification—for example, the tags are laid out in a shape (e.g., a circle, a square, etc.) or pattern (e.g., checkerboard, bar code, etc.) that is detectable using an imaging device. In some embodiments, the shape or shapes of one or more than one of the tags themselves are characterized and the characterization is used for identification. In some embodiments, individual tag placement is partially variable due to inclusion of a random or pseudorandom step in the tag placement process, allowing unique or nearly unique tag placement for each cluster of tags. In some embodiments, the verifier measures the location of one or more tags on an item or label, and from the tag locations and/or shapes produces a signature by means of an algorithm. In some embodiments, the algorithm uses the relative arrangement and/or shape of multiple tags with or without a fiducial mark to produce a single item signature. In some embodiments, the algorithm produces a signature from the location and/or shape of each tag, and then combines the signatures from more than one tag on an item into a single signature. In some embodiments, the algorithm produces multiple signatures derived from the location and/or shape of one or more tags. In some embodiments, the verifier produces a single signature from the location and/or shape of one or more tags. For example, the use of a tag shape or combination of tag shapes, the placement of one or more tags in a pattern or arrangement or the relative locations of the one or more tags, or the spectral signature of a tag or of more than one tag are used alone or in combination to determine whether or not an item marked with the tag(s) is the authentic item.

In some embodiments, tags are made of the silica (deemed "generally recognized as safe"—or GRAS—by the FDA), rendering them biologically inert and edible. Each barely visible tag contains a custom-manufactured spectral signature chosen from over one billion possibilities, yet each item costs only fractions of a penny to label. The unique optical signature of each tag can be read by a low cost scanner and be linked to a label in a secure database, where additional information about the item can be stored, such as referencing a future e-pedigree track-and-trace system. Tags comprise a silicon wafer that is etched to have a spectral code encoded by the etching. The wafer is divided into small tags, and the resultant tags contain a complex porous nanostructure that is programmed during electrochemical synthesis to display a unique reflectivity spectrum. The tags are then oxidized by a high-temperature bake step to turn the crystalline, nanoporous silicon tags into amorphous, nanoporous silica. This bake step stabilizes the nanoporous structure against further oxidation (thus stabilizing the spectral signature) and provides for the tags to be characterized as a GRAS excipient. The spectrum is measured via a simple, low-cost spectrometer-based reader, then quickly verified against other information printed on the package, such that the medicine and packaging are authenticated together; tampering with either the package, or the contents, would flag a security violation. The tags can also be used on their own acting simply as labels for quality assurance or other purposes. Information capacity is projected to potentially reach one trillion possible unique spectra, using peak number, peak placement, peak rugate phase, and/or peak amplitude as modulation parameters. The tags are passive, inconspicuous and can be attached to the outside of medicines or food products to be read, for example, through clear or translucent plastic blister packs, or mixed into medicines or food as a forensic excipient, to be read as part of an investigation or inspection process by authorized security or quality assurance personnel.

In some embodiments, the tag properties comprise:
More than one billion codes available
Inconspicuous size range (20 μm to 150 μm) allows covert or semi-covert use
Made from clear, high purity silica rendering them biologically inert and edible
High temperature resistance—melting point above 1600° C.
Passive—no energy input or output
Can be used in or on a product, package, label, or security fiber
Can be applied via sprays, coatings, inks, varnishes, or as part of laminate
Can be integrated at a number of manufacturing stages—will not slow FDA approvals
High level of security possible using random tag shapes; security can be scaled to suit specific product needs
Can be made self-authenticating and reduce the costs and security risks associated with online databases and maintenance
Each piece of the silica microtag contains the coded information, useful for forensics In some embodiments, a system for manufacturing a label comprises a tag reader a computer, and a label writer. The tag reader determines an identifier based at least in part on a data read by the tag reader. The computer receives an identifier, a key, and a goods information and provides a message authentication code. The label writer receives the message authentication code and provides a label.

FIG. 1 is a block diagram illustrating an embodiment of a package producer. In the example shown, package producer 100 comprises identifier adder 102, labeler 104, and packager 106. Identifier adder 102 receives an identifier (e.g., tag(s)) and item(s) and adds the identifier to the item(s). In some embodiments, the identifier adder 102 is part of an item manufacturing system. In some embodiments, the identifier adder 102 is placed prior to or after item manufacturing. The item with identifier is measured by labeler 104 for spectral information from the tag, placement information of the tag on the item (e.g., in a pattern, in a code, forming a shape, etc.), and tag shape and/or characteristic information. Labeler 104, based on the information detected from the items and/or key and/or goods information, generates a label for a package for the item. Label is added to the package using packager 106. In some embodiments, labeler 104 also sends some or all information to a database handler.

Figure 2:
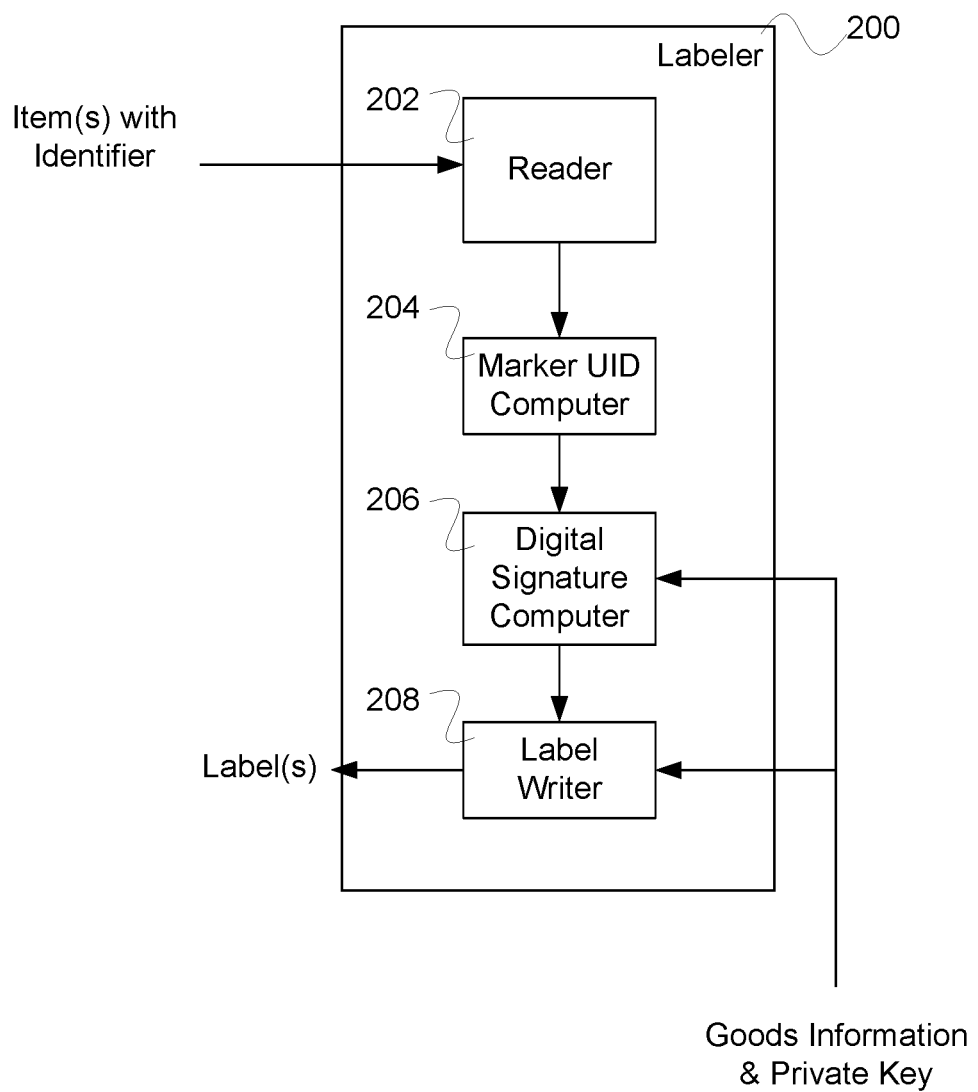
FIG. 2 is a block diagram illustrating an embodiment of a labeler.

FIG. 2 is a block diagram illustrating an embodiment of a labeler. In some embodiments, labeler 200 is used to implement labeler 104 of FIG. 1. In the example shown, labeler 200 comprises reader 202, marker UID computer 204, digital signature computer 206, and label writer 208. Labeler 200 receives item(s) with identifier and goods information and a private key and provides label(s). Reader 202 reads identifier associated with item(s). Reader 202 reads an item using a plurality of reading methods so that an item's tag and/or an item's placement and/or type of item are read. Marker UID computer 204 calculates a marker unique identifier, which comprises information about spectral content, spatial arrangement and/or shape of tags composing the marker. Digital signature computer 206 computes a digital signature using goods information (e.g., information regarding the item) and the marker UID. In some embodiments, Digital signature computer 206 is omitted, and the marker UID is passed directly to label writer 208. Label writer 208 writes a label including machine readable (e.g., 1-dimensional and/or 2-dimensional bar codes) and human readable (e.g., an alphanumeric printed codes and/or other printed characters) features and/or symbols.

Figure 3:
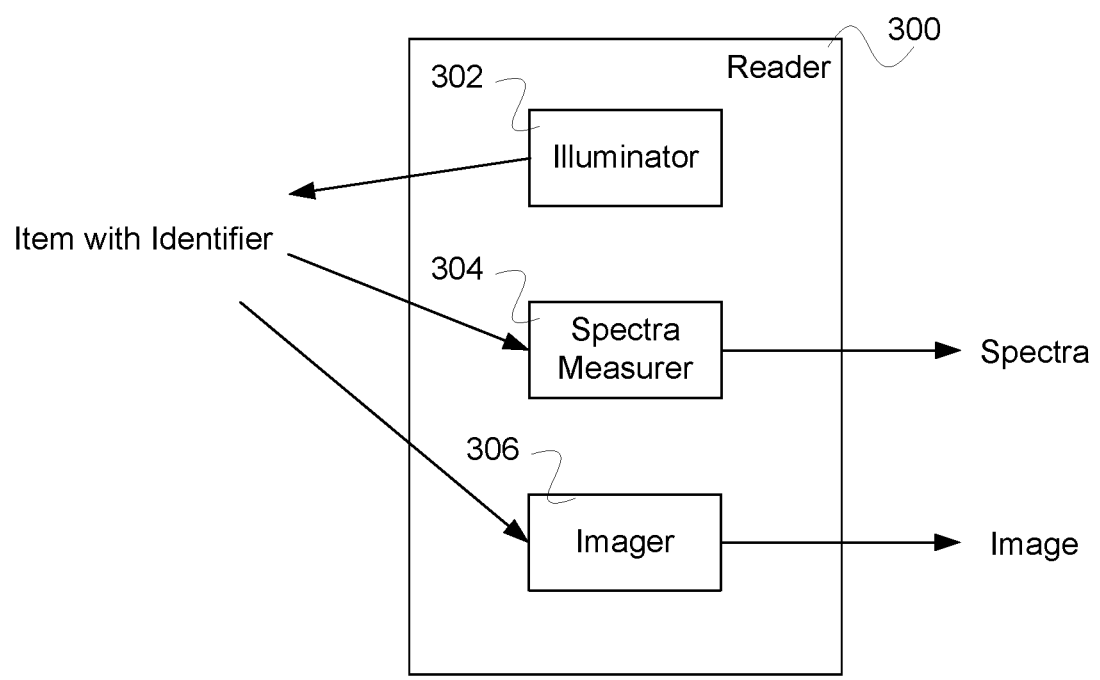
FIG. 3 is a block diagram illustrating an embodiment of a reader.

FIG. 3 is a block diagram illustrating an embodiment of a reader. In some embodiments, reader 300 is used to implement reader 202 of FIG. 2. In the example shown, reader 300 comprises illuminator 302, spectra measurer 304, and imager 306. Reader 300 examines an item with an identifier and provides an output spectra and image. Illuminator 302 illuminates the item enabling the item to be read. In various embodiments, illuminator 302 illuminates with different illumination for spectra measurer 304 (e.g., broadband illumination), for imager 306 (e.g., white light, monochromatic light, etc.), or any other appropriate illumination. Spectra measurer 304 measures the reflectance or transmission spectral response of an item with an identifier. For example, the spectral peaks, their amplitudes (e.g., relative or absolute amplitudes), their frequencies are measured. Imager 306 images the item with an identifier—For example, a placement or shape information associated with the tag placed in item (e.g., a shape or a relation to a fiducial). In some embodiments, imager 306 is omitted from reader 300. In some embodiments, spectra measurer 304 is omitted from reader 300.

Figure 4:
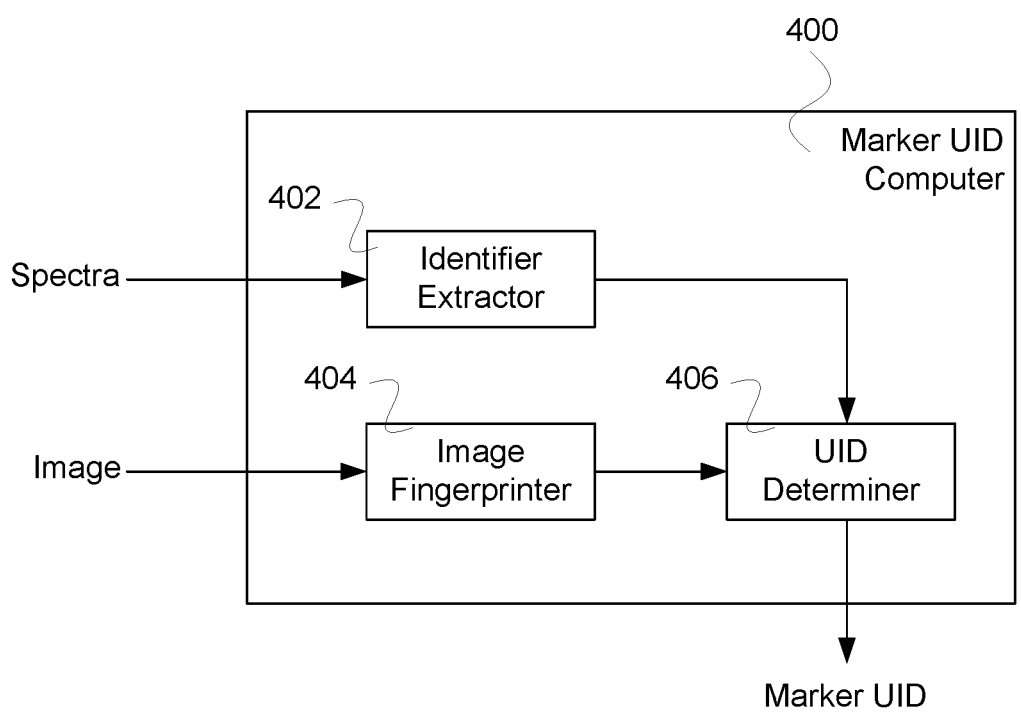
FIG. 4 is a block diagram illustrating an embodiment of a Marker UID computer.

FIG. 4 is a block diagram illustrating an embodiment of a Marker UID computer. In some embodiments, marker UID computer 400 is used to implement marker UID computer 204 of FIG. 2. In the example shown, marker UID computer 400 comprises identifier extractor 402, image fingerprinter 404, and UID determiner 406. Marker UID computer 400 receives spectra and image information and provides a Marker UID. Identifier extractor 402 extracts identifier from spectra information of identifier (e.g., a tag) associated with the item. Image fingerprinter 404 extracts information associated with tag shape or placement information. UID determiner 406 determines a UID based on identifier extracted from spectra and image extracted information. In some embodiments, identifier extractor 402 is omitted, and UID determiner 406 uses only the output of image fingerprinter 404. In some embodiments, image fingerprinter 404 is omitted, and UID determiner 406 uses only the output of identifier extractor 402.

Figure 5:
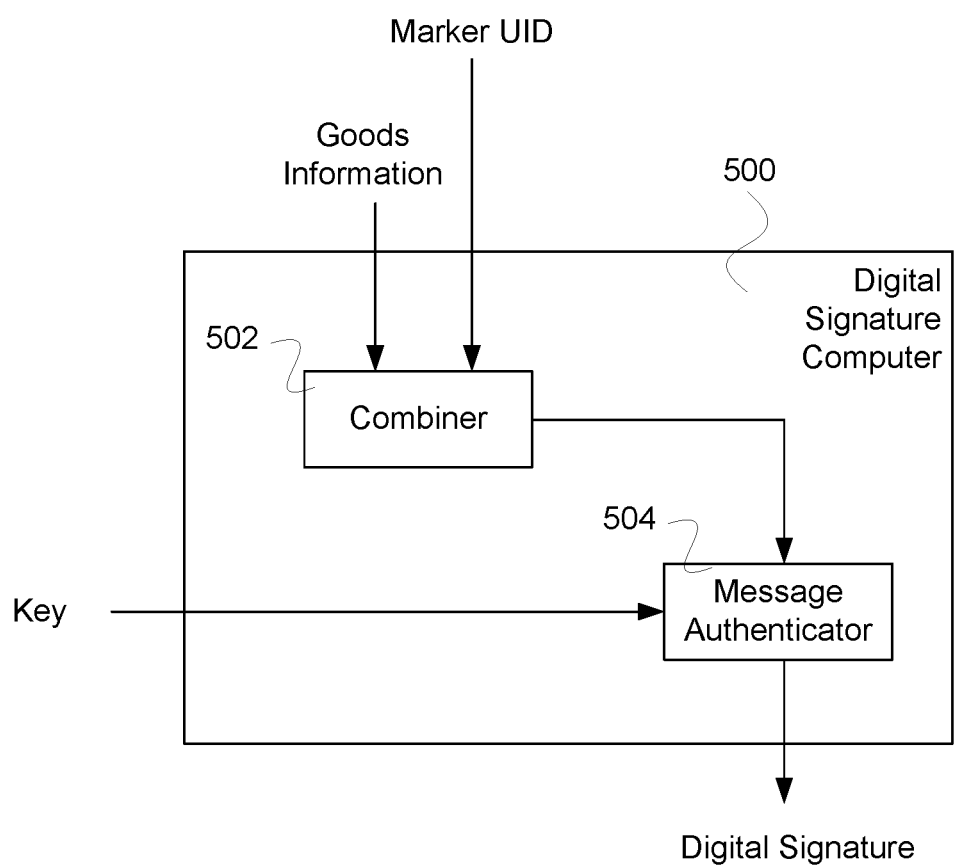
FIG. 5 is a block diagram illustrating an embodiment of a digital signature computer.

FIG. 5 is a block diagram illustrating an embodiment of a digital signature computer. In some embodiments, digital signature computer 500 is used to implement digital signature computer 206 of FIG. 2. In the example shown, digital signature computer 500 comprises combiner 502 and message authenticator 504. Digital signature computer 500 receives goods information and marker UID and a key and provides a message authentication code. Combiner 502 combines goods information and marker UID. Message authenticator 504 digitally signs the output of combiner 502 using a key, and outputs the result.

Figure 6:
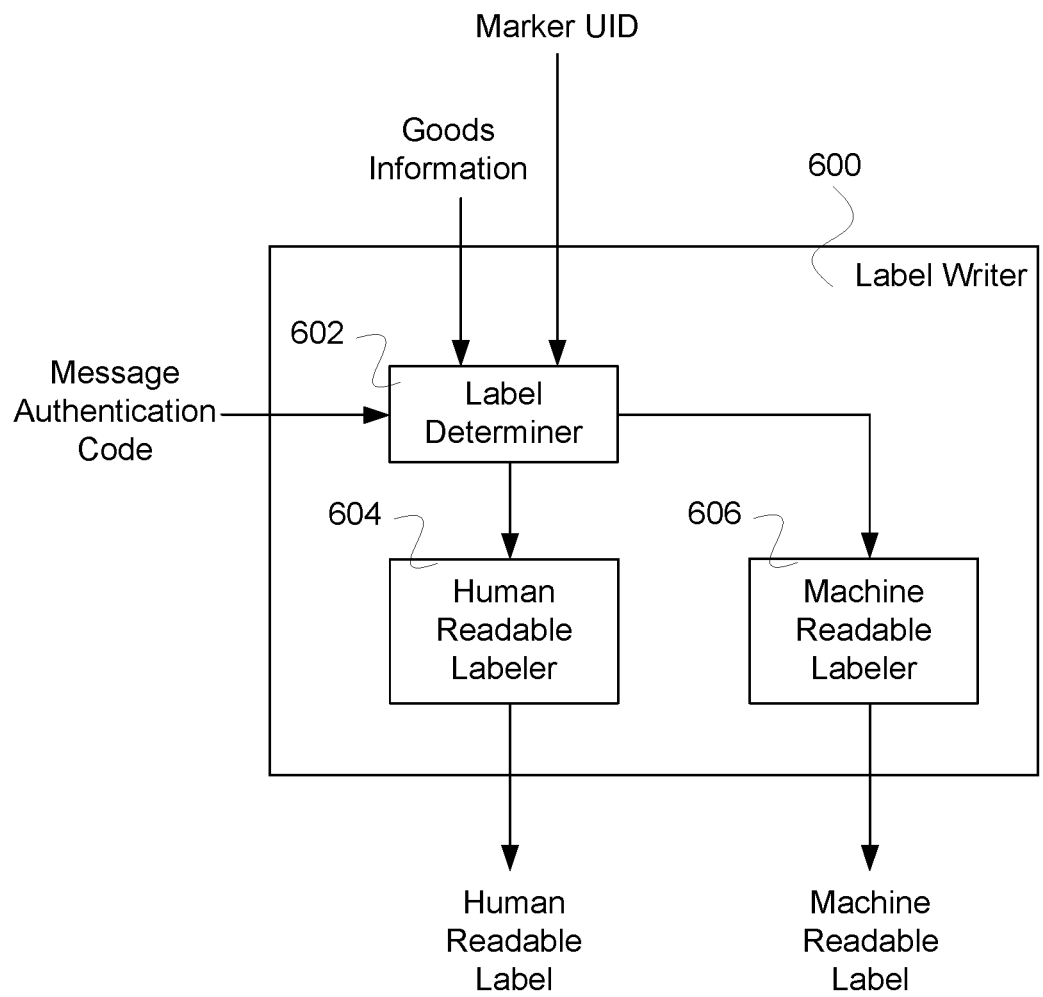
FIG. 6 is a block diagram illustrating an embodiment of a label writer.

FIG. 6 is a block diagram illustrating an embodiment of a label writer. In some embodiments, in 600 label writer is used to implement labeler 104 of FIG. 1. Label writer 600 comprises a label determiner 602, human readable labeler 604, and machine readable labeler 606. Label writer 600 receives a marker UID, goods information, message authentication code and provides a human readable label and a machine readable label. Label determiner 602 receives a marker UID, goods information, optionally message authentication code and determines a human readable label and a machine readable label. Human readable labeler 604 provides a human readable label—for example, a label is produced with alphanumeric codes or an understandable image or combination of the two or with any other appropriate human decodable label. Machine readable labeler 606 provides a machine readable label—for example, a label is produced with a 1-d or 2-d barcode. In some embodiments, label writer 600 also outputs label determiner 602 output to a secure database.

Figure 7:
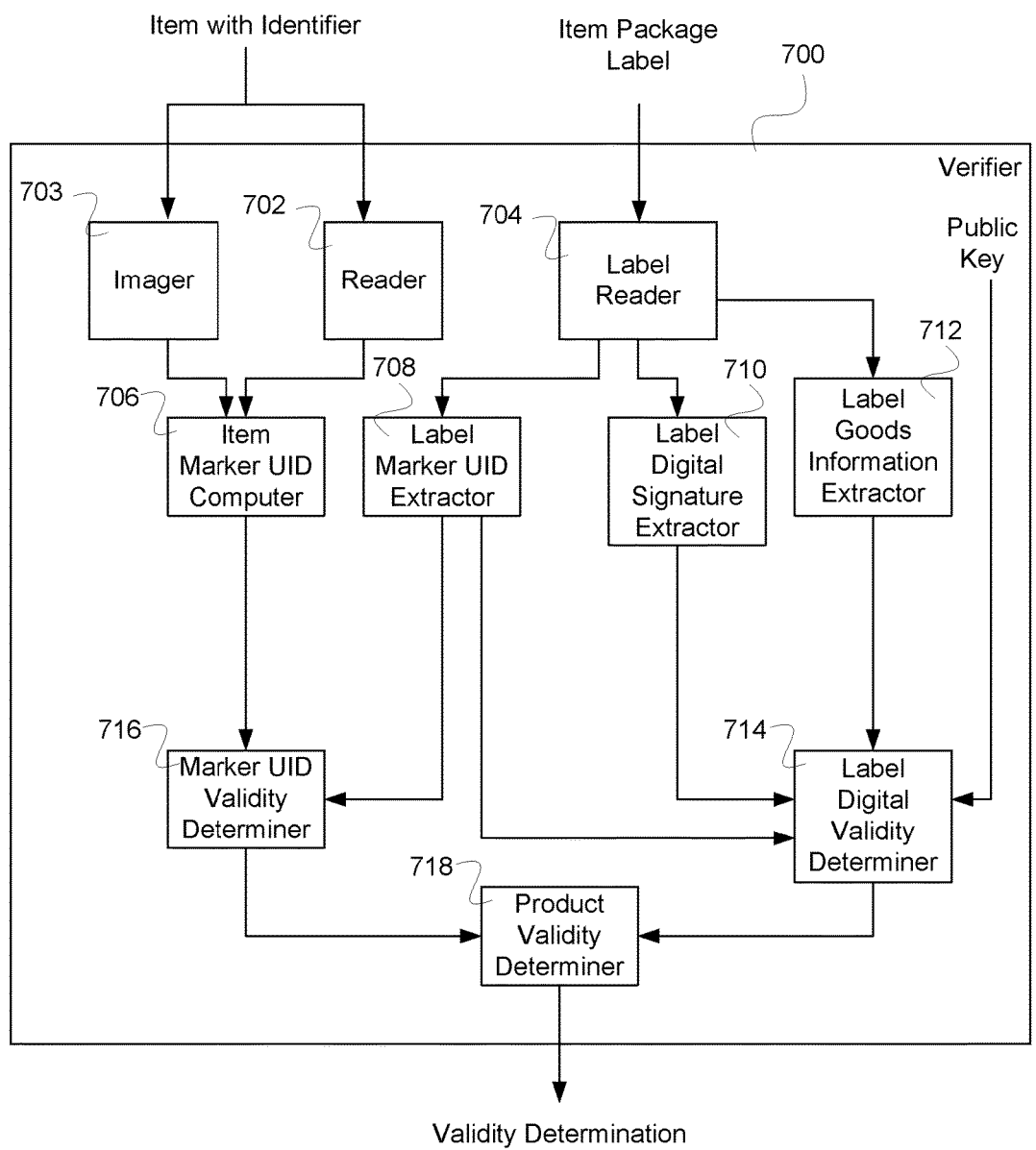
FIG. 7 is a block diagram illustrating an embodiment of a verifier.

FIG. 7 is a block diagram illustrating an embodiment of a verifier. In the example shown, verifier 700 comprises imager 703, reader 702, label reader 704, item marker UID computer 706, label marker UID extractor 708, label digital signature extractor 710, label goods information extractor 712, label digital validity determiner 714, Marker UID validity determiner 716, and product validity determiner 718. Verifier 700 operates on an item with an identifier and on a package with a label and provides a validity determination. Imager 703 and reader 702 extract information by measuring one or more spectra of at least one information tag and an image of the position and/or shape of at least one of the information tags. Item marker UID computer 706 receives the information from imager 703 and reader 702 and determines a marker UID. Label reader 704 reads an item package label and extracts information. Label marker UID extractor 708 receives the information and determines the marker UID. Marker UID validity determiner 716 determines the validity of the marker UIDs produced by label marker UID extractor 708 and item marker UID computer 706. Label reader 704 also determines information for label digital signature extractor 710 and label goods information extractor 712. Label digital validity determiner 714 receives information from label goods information extractor 712, label digital signature extractor 710, label marker UID extractor 708, and public key to determine the validity of the digital signature received from label digital signature extractor 710. Product validity determiner 718 receives UID validity and label digital validity information and produces a product validity determination.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for labeling, comprising:
one or more processors configured to:
read a tag identifier associated with an item;
calculate a marker unique identifier based at least in part on the tag identifier associated with the item;
compute a digital signature based at least in part on the marker unique identifier and goods information, wherein the digital signature is signed using a key; and
write a label, wherein the label has a portion that is readable by a human being and a portion that is readable by a machine, wherein the label is based at least in part on the digital signature, the marker unique identifier, and the goods information and wherein the label is used for authentication.

2. The system as in claim 1, wherein the tag identifier is based at least in part on a shape of a spatial arrangement of tags.

3. The system as in claim 2, wherein the shape comprises a circle or a square.

4. The system as in claim 1, wherein the tag identifier is based at least in part on a pattern of a spatial arrangement of tags.

5. The system as in claim 4, wherein the pattern comprises a checkerboard or a bar code.

6. The system as in claim 1, wherein the tag identifier has a random or pseudorandom spatial arrangement.

7. The system as in claim 1, wherein the label includes a fiducial mark.

8. The system as in claim 1, wherein the authentication is based at least in part on an ingredient.

9. The system as in claim 1, wherein the authentication is based at least in part on a SKU number.

10. The system as in claim 1, wherein the authentication is based at least in part on a physical characteristic.

11. The system as in claim 1, wherein the authentication is based at least in part on a nutrition information.

12. The system as in claim 1, wherein the tag identifier comprises an etched silicon tag.

13. The system as in claim 1, wherein the tag identifier contains a porous nanostructure.

14. A method for labeling, comprising;
reading a tag identifier associated with an item;
calculating, using a processor, a marker unique identifier based at least in part on the tag identifier associated with the item;
computing a digital signature based at least in part on the marker unique identifier and goods information, wherein the digital signature is signed using a key; and
writing a label, wherein the label has a portion that is readable by a human being and a portion that is readable by a machine, wherein the label is based at least in part on the digital signature, the marker unique identifier, and the goods information and wherein the label is used for authentication.

15. A computer program product for labeling, the computer program product being embodied in a non-transitory computer readable storage medium and comprising computer instructions for:
reading a tag identifier associated with an item;
calculating, using a processor, a marker unique identifier based at least in part on the tag identifier associated with the item;
computing a digital signature based at least in part on the marker unique identifier and goods information, wherein the digital signature is signed using a key; and
writing a label, wherein the label has a portion that is readable by a human being and a portion that is readable by a machine, wherein the label is based at least in part on the digital signature, the marker unique identifier, and the goods information, and wherein the label is used for authentication.

* * * * *

UNITED STATES PATENT AND TRADEMARK OFFICE
CERTIFICATE OF CORRECTION

PATENT NO. : 10,490,108 B2
APPLICATION NO. : 15/423337
DATED : November 26, 2019
INVENTOR(S) : Ting Zhou et al.

Page 1 of 1

It is certified that error appears in the above-identified patent and that said Letters Patent is hereby corrected as shown below:

In the Claims

In Column 8, Claim 1, Line 5, after "information", insert --,--
In Column 8, Claim 14, Line 45, after "information", insert --,--

Signed and Sealed this
Twenty-third Day of June, 2020

Andrei Iancu
*Director of the United States Patent and Trademark Office*